(12) United States Patent
Hagiwara

(10) Patent No.: US 6,303,930 B1
(45) Date of Patent: Oct. 16, 2001

(54) COORDINATING OPTICAL TYPE OBSERVING APPARATUS AND LASER MARKING METHOD

(75) Inventor: Ryoji Hagiwara, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/310,766

(22) Filed: May 13, 1999

(30) Foreign Application Priority Data

May 14, 1998 (JP) .................................................. 10-131865

(51) Int. Cl.[7] .............................. G01N 23/00; G21K 7/00
(52) U.S. Cl. ............................................................. 250/306
(58) Field of Search ............................... 250/561, 559.41, 250/306, 559.45; 382/151; 346/160; 356/237, 432; 351/221

(56) References Cited

U.S. PATENT DOCUMENTS

| | | | |
|---|---|---|---|
| 5,028,939 | * | 7/1991 | Hornbeck et al. .................... 346/160 |
| 5,715,052 | * | 2/1998 | Fujino et al. ......................... 356/237 |
| 6,081,614 | * | 6/2000 | Yamada et al. ....................... 382/151 |

FOREIGN PATENT DOCUMENTS

| | | |
|---|---|---|
| 57-55947 | 9/1955 | (JP) . |
| 9283073 | * 10/1997 | (JP) . |

\* cited by examiner

Primary Examiner—Jack Berman
Assistant Examiner—Johnnie L Smith, II
(74) Attorney, Agent, or Firm—Adams & Wilks

(57) ABSTRACT

An optical observing apparatus has a sample stage for moving a sample to a desired location to be operated upon at a target position by a charged particle beam apparatus so that the target position can be visually observed, an optical observation system for magnifying the sample for visual observation of the target position, a marking system for moving the sample based on the visual observation and marking the sample at one or more locations from which the target position can be determined without the need for further visual observation so that the target position may be located by the charged particle beam apparatus even when the target position can not be visually observed by use of the charged particle beam apparatus, and a control system for storing the target position and the location of the one or more markings together with an optical observation image and corresponding stage coordinate. In a preferred embodiment, the marking system is a laser marking system for producing a plurality of laser beams on the same optical axis, each having a different wavelength, so that an appropriate laser beam may be selected based upon the nature of the sample. The sample has an underlying structure covered by a layer of transparent material, so that the underlying structure can be visually observed by means of the optical observation system but cannot be observed by use of the charged particle beam apparatus.

16 Claims, 3 Drawing Sheets

COORDINATING OPTICAL TYPE OBSERVING APPARATUS AND LASER MARKING METHOD

BACKGROUND OF THE INVENTION

The present invention relates to an observation position and forming position determining method in an observation/forming apparatus using a charged particle apparatus such as a focused ion beam apparatus FIB (Focused Ion Beam) scanning electron microscope (SEM), and to an apparatus therefor.

The conventional FIB/SEM observation position alignment utilizing an optical microscope image includes two methods. The first is a method of comparing two images to align them on a coordinate and performing marking with an FIB to enable location of a mark position by use of an optical microscope, thereby confirming the position. The second is a method for aligning positions of an optical microscope image and an FIB and SEM image from a coordinate relationship. For example, such a method is disclosed in JP-A-9-097585.

There is a problem in that the above described technology in damage is caused to a sample due to FIB/SEM and labor and time is required in forming position specifying time and also in detailed position specifying accuracy to conduct section observation.

For example, in a semiconductor manufacturing process, highly integrated semiconductor manufacture has recently been obtained in multi-layer structures using planar layers as interconnect line width has been reduced. On the semiconductor surface a transparent passivation film is formed. Due to this, because the passivation film does not transmit electrons or ions, it has become impossible to observe a target position inside the planarized film after planarization. Accordingly, optical observation images are required to supplement positioning observation/forming position location for FIB/SEM use. However, the section forming of an interconnect of 1 micron or smaller requires observation/forming position alignment of 1 micron or less. However, there is a problem in that using only stage coordinate movement positioning an accuracy of 1 micron or smaller is difficult to easily achieve.

Also, there is a problem of occurrence of reference (contamination) on a sample encountered in long time or strong electron/ion beam observation.

It is an object of the present invention to provide an apparatus which is capable of improving observation/forming position positional accuracy using FIB/SEM and reducing sample damage by an electron/ion beam due to observation time shortening.

SUMMARY OF THE INVENTION

A coordinating optical type observing apparatus of the present invention sets a sample on a stage and moves it to a target position while observing at an external coordinate or continuous optical image.

A laser marking method of the present invention performs marking of a diameter of 10 microns or smaller by selecting a proper laser oscillation wavelength based on a sample nature by a laser optical system coaxially arranged with respect to an optical observing system on both sides of a target position to be observed and formed with an FIB or SEM.

Further, the coordinating optical type observing apparatus of the present invention can accumulate on a recording medium, together with a positional coordinate, an optical image at a position at which marking was made.

Also, the accumulated data is read from an external FIB/SEM, which can be used to search a target position.

Because the present invention searches for a target position by use of an optical image, there is no damage caused by irradiating a laser beam such as in FIB or SEM onto the sample. Further, because the material of a planarized film used in a semiconductor manufacturing process can transmit in the optical type observing apparatus, where a target position for observing/forming of FIB/SEM is under the planarized film, the position can be specified. Also, an optical type observing image can be distinguished in target position due to color, different from an image of an FIB/SEM.

Next, by performing marking of 10 microns or smaller on both sides of the target position, the target position of forming and observing for FIB/SEM can be specified with an accuracy of 1 micron or less.

Also, the present invention can accumulate in a recording medium laser-marked position information and an optical image and positional coordinate including the laser mark. This accumulated information can be supplied as observation/forming information for other observation/forming and semiconductor manufacturing apparatus performed by an FIB/SEM.

DETAILED DESCRIPTION OF THE INVENTION

In the discussion below, an embodiment of the present invention is explained with reference to the accompanying drawings.

Figure 1:
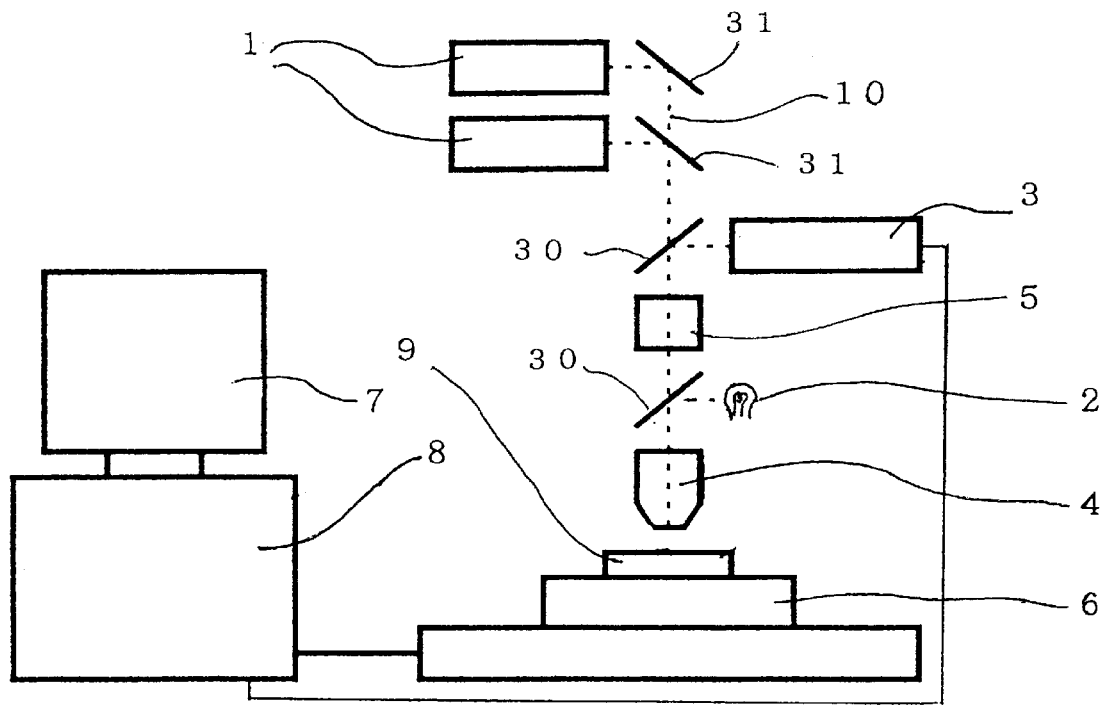
FIG. 1 is a schematic sectional view of an apparatus showing an embodiment of an optical type observing apparatus of the present invention.

FIG. 1 is a schematic diagram showing a coordinating optical type observation apparatus of the present invention. Explanation is made below according to the drawings.

A sample 9 for observing/forming by an FIB/SEM serving as a charged particle apparatus is placed at a center on a stage 6 of an optical type observation apparatus. The optical type observation apparatus is provided with a sample illumination lamp 2 to illuminate light to a surface of the sample 9. The light from the sample illumination lamp 2 illuminates the sample 9 surface through a half mirror 30. The sample 9 placed on the stage 6 is observed by CCD 3 through an optical image observation system formed by an objective lens 4, an ocular lens 5 and a half mirror 30. The image of the sample 9 surface taken by the CCD 3 is fetched in real time by a control system 8 and displayed on CRT 7. Here, for observing the sample 9 with magnification the sample illumination lamp 2, the half mirror 30, the objective lens 4 and ocular lens 5 and the CCD 3 are collectively referred to as an optical system lens barrel. The operator uses an operation screen present on the control system 8 to control the stage 6, searching for a target position. The operation screen present on this control system 8 can be provided on a CRT 7. Also, a plurality of laser light sources 1 are provided respectively to irradiate laser light onto the sample 9 surface through a laser half mirror 31. An observation optical axis 10 for observing the sample 9 and a laser irradiation optical axis 10 are in a coaxial relation with respect to each other. The plurality of laser light sources 1 are provided with a not-shown device for position adjustment so that laser is irradiated to a center position of the sample 9 image displayed on the CRT 7.

At this time, the control system 8 uses an auxiliary function capable of referring to coordinate information from other devices, also performing reduction in moving time in search.

After moving to the target position, laser irradiation is carried out from the laser light source 1 coincident with the optical axis of the observation optical system to put a mark 13 on the sample 9 placed on the stage. Lasers different in wavelength are arranged on the same optical axis 10 such that an appropriate wavelength can be selected for the mark 13 depending on the sample 8 material.

For the sample 9 provided with the mark 13, an image with a mark and stage coordinate are accumulated in the control system 8. The accumulated data can be output to a network.

Figure 2:
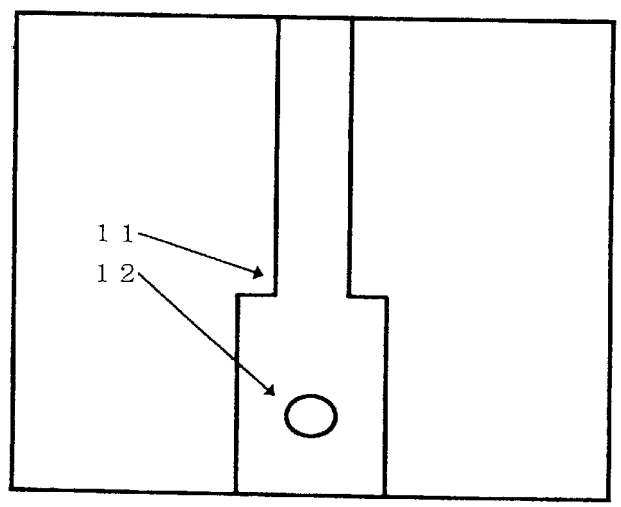
FIG. 2 is a plan view of an optical observation image for explaining an observation embodiment of the present invention.
Figure 3:
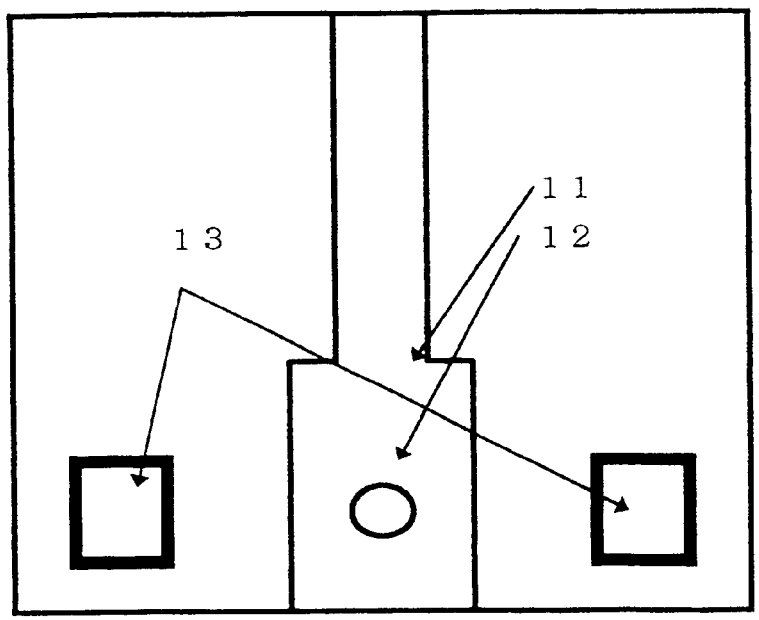
FIG. 3 is a plan view of an optical observation image for explaining an observation embodiment of the present invention.
Figure 4:
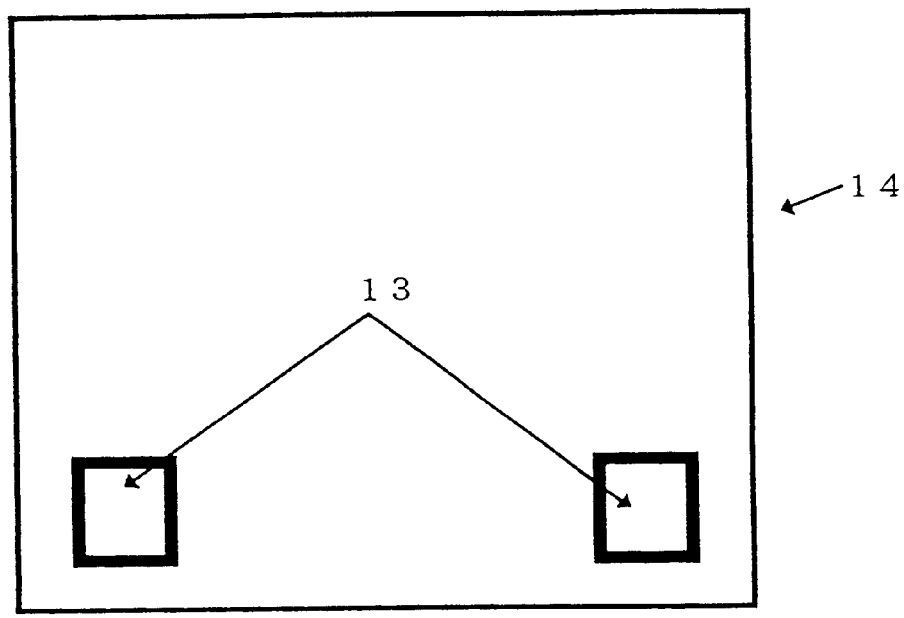
FIG. 4 is a plan view of an optical observation image for explaining an observation embodiment of the present invention.

Next, an explanation is provided of the marking by reference to FIG. 2 to FIG. 4.

For the planarized sample 9, a structure 11 under a passivation film is observed together with the passivation film 14 through optical observation on the CRT 7, as shown in FIG. 2. Considering the size of an object to be observed/processed present at a target position 12 based on this observation image, a mark 13 is applied by laser from the laser light source 1 as shown in FIG. 3. As for two marks 13, 13, marks 13, 13 are formed in position at almost equal distance with respect to a forming position center as a center.

The apparatus of the present invention determines a center of gravity of each mark through image processing from this mark. Two centers of gravity are taken for a line fragment to determine from the optical observation image whether the center of the line fragment is deviated from the forming/observing position. As a coordinate of the observation/forming position, storage is made together with the laser-marked image in the control system 8.

The positioning accuracy of the observing/forming position can be rendered to ½ of an oscillation wavelength of the laser used for marking, where the laser mark size is such that the sample can absorb the laser wavelength. Accordingly, the observing/forming position as a target can be approximately ⅒ of the mark size. Also, even where the mark center position is taken as the observing/forming position without image processing, the amount of positional deviation can be rendered about ½ of the mark size.

In the case where observation of a target position is made by an FIB/SEM in a manner avoiding sample damage due to an electron/ion beam based on the information taken in the above procedure, an image shown in FIG. 4 is observed. The interconnect 11 formed under the passivation film 14 cannot be observed. That is, the image observed is only the passivation film 14 surface 1 and the two marks 13. From this observation image, a center position of the mark is determined by the above-mentioned method. It is possible to observe through an electron beam raised in acceleration voltage or form the target position 12 by a focused ion beam with a positioning accuracy of less than 1 micron.

Figure 5:
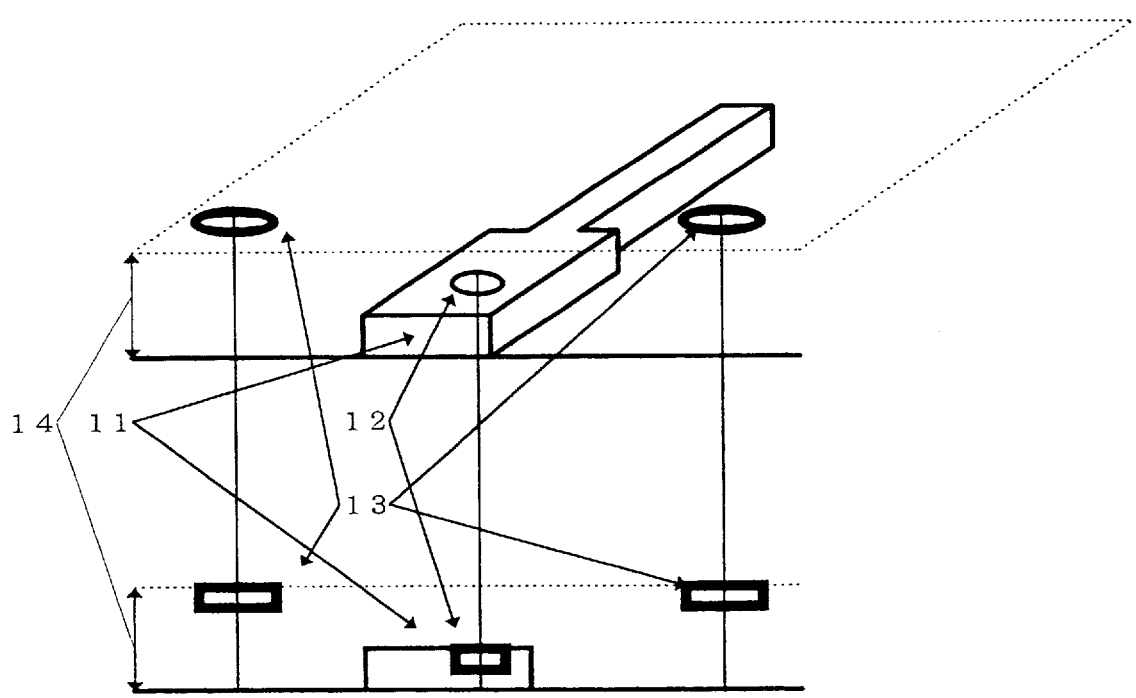
FIG. 5 is a perspective view and sectional view of a sample for explaining an observation embodiment of the present invention.

The relationship between the above mark and target position is three-dimensionally shown in FIG. 5. As shown in FIG. 5, the passivation film 14 covers the interconnect 11. The surface of the passivation film 14 is flat except for the laser mark 13 and cannot be observed by the electron/ion beam. The apparatus of the present invention is made to match the laser output and wavelength to a material of the passivation film 14 (planarized film) to adjust/change an output from the known information in order to prevent affection of the laser mark on the underlayer structure.

As described above, according to the present invention the specifying of a sample observation/forming position having a planarized film without roughening on a sample surface, that could not be made by FIB/SEM, is made from an actual image in contrast to a case of performing only a stage coordinate. Accordingly, even with an apparatus not high in stage coordinate accuracy, it is possible maximally up to one-tenth of a size of a laser mark. Further, because long time observation by FIB/SEM can be avoided, it is possible to suppress damage to a sample by an electron/ion beam to a narrow region and minimally.

Also, by selecting a laser wavelength and performing marking, damage to a sample state can be reduced to a minimum.

That is, it is very effective in positioning of a forming position for a sample that has been difficult to specify an observation/forming position by FIB/SEM.

What is claimed is:

1. An optical observing apparatus, comprising: a sample stage for supporting a sample to be observed or acted upon at a target position by a charged particle beam generating apparatus and moving the sample to a desired stage coordinate at which the target position may be visually observed; an optical observation system for magnifying the sample for visual observation of the target position and having an optical observation axis; a laser marking system having an axis arranged coaxially with the optical observation axis for moving the sample based on the visual observation and marking the sample with a laser at one or more locations from which the target position can be determined without the need for further visual observation, so that the target position may be located by the charged particle beam apparatus even when the target position can not be visually observed by use of the charged particle beam apparatus; and a control system for storing the target position and the location of the one or more laser markings as an optical observation image together with a corresponding stage coordinate.

2. An optical observing apparatus according to claim 1; wherein the laser marking system marks the sample at more than one position separated from the target position and from which the target position may be determined; and further comprising image processing means for determining a center of gravity of each of the marks applied on the sample by the laser marking system to locate the target position based on the center of gravity of the marks.

3. A laser marking method, comprising the steps of: moving a stage supporting a sample according to stage coordinate data from an external device such that laser marking may be conducted at a location on the sample from which a target position on the sample to be worked on by a charged particle beam of a charged particle beam apparatus may be determined; applying one or more laser markings at the location using a laser marking system arranged coaxially with the optical observation system; and using an optical observation system having an optical axis coaxially aligned with the optical axis of the laser marking system for storing a magnified visual image of the sample containing the one or more laser markings and an image of the sample including the target position together with the stage coordinate.

4. An optical observing apparatus according to claim 1; wherein the charged particle beam apparatus is at least one of a focused ion beam apparatus and a scanning electron microscope.

5. An optical observing apparatus according to in claim 1; wherein the control system is connected to the charged particle apparatus to set one of an observing region and a forming region for use by the charged particle apparatus based on the stage coordinate corresponding to the stored optical observing image.

6. An optical observing apparatus according to claim 1; wherein the laser marking system emits a plurality of laser beams of different wavelength on the same optical axis.

7. An optical observing apparatus according to claim 1; wherein the sample has an underlying structure covered by a layer of transparent material, so that the underlying structure can be visually observed by means of the optical observation system but cannot be observed by use of the charged particle beam apparatus.

8. An optical observing apparatus according to claim 1; wherein the optical observation system comprises a lamp for illuminating the sample, a plurality of lenses, a CCD camera for obtaining an image for the lenses, and a display device for displaying an image of the sample.

9. An optical observing apparatus, comprising: a sample stage for supporting a sample to be operated upon at a target position by a charged particle beam produced by a charged particle beam apparatus, the sample stage being movable to position the sample to a desired stage coordinate at which the target position may be visually observed; an optical observation system for magnifying the sample for visual observation of the target position and having an optical observation axis; a marking system having an axis aligned coaxially with the optical observation axis for moving the sample based on the visual observation and marking the sample at one or more locations from which the target position can be determined without the need for further visual observation, so that the target position may be located by the charged particle beam apparatus even when the target position can not be visually observed by use of the charged particle beam apparatus; and a control system for storing the target position and the location of the one or more markings together with an optical observation image and corresponding stage coordinate.

10. An optical observing apparatus according to claim 9; wherein the marking system marks the sample at more than one position separated from the target position and from which the target position may be determined; and further comprising image processing means for determining a center of gravity of each of the marks applied on the sample by the laser marking system to locate the target position based on the center of gravity of the marks.

11. An optical observing apparatus according to claim 9; wherein the marking system comprises a laser marking system.

12. An optical observing apparatus according to claim 9; wherein the sample has an underlying structure covered by a layer of transparent material, so that the underlying structure can be visually observed by means of the optical observation system but cannot be observed by use of the charged particle beam apparatus.

13. An optical observing apparatus according to claim 9; wherein the optical observation system comprises a lamp for illuminating the sample, a plurality of lenses, a CCD camera for obtaining an image from the lenses, and a display device for displaying an image of the sample.

14. An optical observing apparatus according to claim 9; wherein the charged particle beam apparatus comprises at least one of a focused ion beam apparatus and a scanning electron microscope.

15. An optical observing apparatus according to in claim 9; wherein the control system is connected to the charged particle beam apparatus to set one of an observing region and a forming region for use by the charged particle beam apparatus based on the stage coordinate corresponding to the stored optical observation image.

16. An optical type observing apparatus according to claim 9; wherein the laser marking system emits a plurality of laser beams of different wavelength on the same optical axis, so that an appropriate laser beam may be selected based upon the nature of the sample.

* * * * *